US012788746B2

(12) United States Patent
Shindo

(10) Patent No.: US 12,788,746 B2
(45) Date of Patent: Nov. 10, 2026

(54) LIQUID-STATE PHARMACEUTICAL COMPOSITION EXHIBITING EXCELLENT PRESERVATIVE EFFECTIVENESS

(71) Applicant: ISHIHARA SANGYO KAISHA, LTD., Osaka (JP)

(72) Inventor: Takeshi Shindo, Osaka (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 637 days.

(21) Appl. No.: 18/246,775

(22) PCT Filed: Sep. 27, 2021

(86) PCT No.: PCT/JP2021/035417

§ 371 (c)(1),
(2) Date: Mar. 27, 2023

(87) PCT Pub. No.: WO2022/071233

PCT Pub. Date: Apr. 7, 2022

(65) Prior Publication Data

US 2023/0372315 A1 Nov. 23, 2023

(30) Foreign Application Priority Data

Sep. 29, 2020 (JP) ................................ 2020-164034

(51) Int. Cl.

*A61K 31/44* (2006.01)
*A61K 47/10* (2017.01)
*A61K 47/26* (2006.01)

(52) U.S. Cl.

CPC .............. *A61K 31/44* (2013.01); *A61K 47/10* (2013.01); *A61K 47/26* (2013.01)

(58) Field of Classification Search

CPC ......... A61K 31/44; A61K 47/10; A61K 47/26
See application file for complete search history.

(56) References Cited

U.S. PATENT DOCUMENTS

| | | | |
|---|---|---|---|
| 6,653,333 | B2 | 11/2003 | Yotsuya et al. |
| 2007/0027119 | A1 | 2/2007 | Ahmed et al. |

FOREIGN PATENT DOCUMENTS

| | | | |
|---|---|---|---|
| EP | 1252890 | A1 | 10/2002 |
| JP | H06263735 | A | 9/1994 |
| JP | 2016-040277 | A | 3/2016 |
| JP | 2016-529242 | A | 9/2016 |
| WO | 01/56568 | A1 | 8/2001 |
| WO | 01/56569 | A1 | 8/2001 |
| WO | 01/56570 | A1 | 8/2001 |
| WO | 2010/137484 | A1 | 12/2010 |
| WO | 2019106573 | A1 | 6/2019 |
| WO | 2019167979 | A1 | 9/2019 |

OTHER PUBLICATIONS

Apr. 13, 2023 (WO) International Preliminary Report on Patentability PCT/JP2021/035417.
Jan. 26, 2025 (CN) Office Action Applicaiton No. 202180066887.2.
"Pre-filled injection technology and application" p. 17, Publication date Apr. 30, 2017, Chief Editor Ma Xianpeng, Published by Shanghai Science and Technology Press (Nonpatent literature) with a machine translation into English.
Apr. 17, 2026 (IN) Office Action Application No. 202317027077.
Apr. 1, 2024 (CL) Office Action Application No. 202300871 with an English translation.
Jun. 5, 2025 (RU) Office Action—App 2023110052.
Jun. 18, 2025 (CN) Office Action—App 202180066887.2.
Jun. 20, 2025 (JP) Office Action—App 2022-553959.
Jan. 29, 2025 (RU) Russian Office Action of Jan. 29, 2025, with an English translation.
Oct. 29, 2025—(PH) Office Action—Appl No. 1/2023/550829.
Benzyl Alcohol Handbook of Pharmaceutical Excipients Eighth Edition (2017).
Jul. 25, 2024 (EP) European Search Report Patent Application No. 21875535.3.
Apr. 18, 2025 (TW) Office Action Application No. 110136251.
Apr. 17, 2026 (MX) Office Action Application No. MX/a/2023/003603.

*Primary Examiner* — Paul V Ward
(74) *Attorney, Agent, or Firm* — Banner & Witcoff, Ltd.

(57) ABSTRACT

An object of the present invention is to enhance preservative effectiveness of a liquid composition containing N-(2-ethylsulfonylamino-5-trifluoromethyl-3-pyridyl)cyclohexanecarboxamide or a salt thereof by using a liquid composition containing N-(2-ethylsulfonylamino-5-trifluoromethyl-3-pyridyl)cyclohexanecarboxamide or a salt thereof, benzyl alcohol and water and having pH of 8 or more.

14 Claims, No Drawings

LIQUID-STATE PHARMACEUTICAL COMPOSITION EXHIBITING EXCELLENT PRESERVATIVE EFFECTIVENESS

REFERENCE TO RELATED APPLICATION

This patent application claims the priority of Japanese Patent Application No. 2020-164034 filed Sep. 29, 2020, the whole contents of which are incorporated herein by reference.

TECHNICAL FIELD

The present invention relates to a liquid composition containing N-(2-ethylsulfonylamino-5-trifluoromethyl-3-pyridyl)cyclohexanecarboxamide exhibiting excellent preservative effectiveness or a salt thereof.

BACKGROUND ART

N-(2-ethylsulfonylamino-5-trifluoromethyl-3-pyridyl)cyclohexanecarboxamide or a salt thereof is known to have phospholipase A2 inhibitory action and be useful as an active ingredient of an anti-inflammatory agent or an anti-pancreatitis agent (Patent Document 1).

Therapeutic agents or prophylactic agents for digestive disorders, liver diseases, pulmonary insufficiency or shock lung, containing N-(2-ethylsulfonylamino-5-trifluoromethyl-3-pyridyl)cyclohexanecarboxamide or a salt thereof as an active ingredient, are also known (Patent Documents 2, 3, 4 and 5).

Further, Patent Documents 1 to 5 disclose compositions for preparations such as an injection, containing the active ingredient mentioned above and also disclose that such compositions may contain an antibacterial agent such as benzyl alcohol.

Benzyl alcohol is an antibacterial agent widely used in injections and optimal antibacterial activity thereof is exhibited at less than pH5 and virtually no antibacterial activity is exhibited beyond pH8 (non-Patent Document 1). Conversely, N-(2-ethylsulfonylamino-5-trifluoromethyl-3-pyridyl)cyclohexanecarboxamide or a salt thereof is virtually not dissolved in water having pH5 or less. Accordingly, contrary to the disclosures of Patent Documents 1 to 5, benzyl alcohol is conceivably not appropriate as an antibacterial agent for a composition containing N-(2-ethylsulfonylamino-5-trifluoromethyl-3-pyridyl)cyclohexanecarboxamide or a salt thereof.

In the meantime, from the viewpoint of convenience for users, it has been desired to use N-(2-ethylsulfonylamino-5-trifluoromethyl-3-pyridyl)cyclohexanecarboxamide or a salt thereof in the form of a composition such as an injection, in particular, a composition filled in a multiple-use vial, for a long period of time. Accordingly, it has been desired to develop technical means for enhancing preservative effectiveness of a liquid composition containing N-(2-ethylsulfonylamino-5-trifluoromethyl-3-pyridyl)cyclohexanecarboxamide or a salt thereof.

CITATION LIST

Patent Documents

Patent Document 1: Japanese Patent Laid-Open No. H06-263735

Patent Document 2: International Publication No. WO2001/056568

Patent Document 3: International Publication No. WO2001/056569

Patent Document 4: International Publication No. WO2001/056570

Patent Document 5: International Publication No. WO2010/137484

Non-Patent Documents

Non-Patent Document 1: Handbook of Pharmaceutical Excipients, eighth edition (2017), p. 105

SUMMARY OF INVENTION

In studies for the invention, the present inventors have found that, when N-(2-ethylsulfonylamino-5-trifluoromethyl-3-pyridyl)cyclohexanecarboxamide or a salt thereof and benzyl alcohol are present together, benzyl alcohol unexpectedly exhibits antibacterial activity even at pH at which benzyl alcohol does not exhibit antibacterial activity, and enhances preservative effectiveness of a liquid composition containing N-(2-ethylsulfonylamino-5-trifluoromethyl-3-pyridyl)cyclohexanecarboxamide or a salt thereof.

Note that, N-(2-ethylsulfonylamino-5-trifluoromethyl-3-pyridyl)cyclohexanecarboxamide (Fuzapladib) is a compound represented by the structural formula of the following formula (1) and hereinafter will be sometimes simply referred to as the compound of formula (1).

[Formula 1]

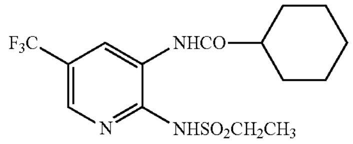

(1)

Accordingly, an object of the present invention is to provide a liquid composition containing N-(2-ethylsulfonylamino-5-trifluoromethyl-3-pyridyl)cyclohexanecarboxamide or a salt thereof and having an enhanced preservative effectiveness.

The following inventions are included in the present invention.

[1] A composition containing:

a compound represented by formula (1) or a salt thereof:

[Formula 2]

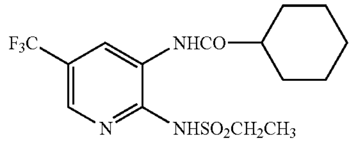

(1)

benzyl alcohol; and water, wherein the composition has pH of 8 or more.

[2] The composition according to [1], further containing a saccharide and, if desired, a pH adjuster.

[3] The composition according to [2], wherein the saccharide is at least one selected from the group consisting of a monosaccharide, a disaccharide, a polysaccharide and a sugar alcohol.

[4] The composition according to [2], wherein the pH adjuster is a buffer.

[5] The composition according to any one of [1] to [4], wherein a content of benzyl alcohol in the liquid composition is 0.9 to 3 w/v %.

[6] The composition according to any one of [1] to [5], wherein a content of the compound of formula (1) or a salt thereof in the liquid composition is 0.01 to 1 w/v %.

[7] The composition according to any one of [1] to [6], for multiple administration.

[8] A kit for producing the composition according to any one of [1] to [7], containing:

a first composition containing the compound of formula (1) or a salt thereof; and a second composition containing benzyl alcohol and water.

[9] The kit according to [8], wherein the first composition contains a saccharide and, if desired, a pH adjuster.

[10] The kit according to [8] or [9], wherein a content of benzyl alcohol in the second composition is 0.9 to 3 w/v % based on the second composition.

[11] The kit according to any one of [8] to [10], wherein the first composition is filled in a vial.

[12] The kit according to [11], wherein the vial is a single-use vial or a multiple-use vial.

[13] The kit according to [11], wherein the vial is a multiple-use vial.

[14] A method for producing the composition according to any one of [1] to [7], including mixing a first composition containing the compound of formula (1) or a salt thereof, and a second composition containing benzyl alcohol and water.

[15] A method for enhancing preservative effectiveness of a liquid composition containing the compound of formula (1) or a salt thereof, including allowing the compound of formula (1) or a salt thereof and benzyl alcohol to be present together in a liquid composition and adjusting pH of the liquid composition to be 8 or more.

According to the present invention, preservative effectiveness in a liquid composition containing the compound of formula (1) or a salt thereof can be effectively enhanced. Accordingly, the composition of the present invention is advantageous since it is used as a composition for multiple administration, for example, a composition filled in a multiple-use vial.

DETAILED DESCRIPTION OF THE INVENTION

The liquid composition of the present invention is characterized by containing N-(2-ethylsulfonylamino-5-trifluoromethyl-3-pyridyl)cyclohexanecarboxamide or a salt thereof and water together with benzyl alcohol, and having pH of 8 or more.

N-(2-ethylsulfonylamino-5-trifluoromethyl-3-pyridyl)cyclohexanecarboxamide or a Salt Thereof N-(2-ethylsulfonylamino-5-trifluoromethyl-3-pyridyl)cyclohexanecarboxamide of the present invention is represented by the structural formula (1).

A salt of the compound of the formula (1) may be any salt can be used as long as it is a pharmaceutically acceptable salt. Examples of the salt include alkali metal salts such as a potassium salt and a sodium salt; alkaline earth metal salts such as a calcium salt; and organic amine salts such as a triethanolamine salt and a tris (hydroxymethyl)aminomethane salt. A salt of the compound of formula (1) may be any one of these salts having crystal water, more specifically, a hydrate thereof.

The compound of formula (1) or a salt thereof can be produced, for example, by a method disclosed in Japanese Patent Laid-Open No. H06-263735.

According to a preferred embodiment of the present invention, the content of the compound of formula (1) or a salt thereof in the composition of the present invention is not particularly limited as long as it does not interfere with the effect of the present invention. The content thereof can be, for example, 0.001 to 15 w/v (mass/volume) % based on the composition, preferably 0.005 to 10 w/v %, more preferably 0.01 to 5 w/v %, further preferably 0.01 to 1 w/v %, and further preferably 0.1 to 1 w/v %. The content of the compound of formula (1) or a salt thereof in the composition of the present invention can be measured by HPLC method, for example, in accordance with the method disclosed in Example 1 of International Publication No. WO2019/167979.

Benzyl Alcohol

In the present invention, benzyl alcohol can be used for providing preservative effectiveness.

According to a preferred embodiment of the present invention, the content of benzyl alcohol in the composition of the present invention is not particularly limited as long as it does not interfere with the effect of the present invention. The lower limit of the content of benzyl alcohol is, for example, 0.8 w/v % or more, preferably 0.9 w/v % or more, and more preferably 1.2 w/v % or more. Whereas, the upper limit of the content of benzyl alcohol is, for example, 5 w/v % or less, preferably 4 w/v % or less, more preferably 3 w/v % or less, and further preferably 2 w/v % or less. Accordingly, the content is, for example, 0.9 to 5 w/v % based on the composition, preferably 0.9 to 4 w/v %, more preferably 0.9 to 3 w/v %, and further preferably 1.2 to 2 w/v %. The content of benzyl alcohol in the composition of the present invention can be measured, for example, by HPLC (method) but other methods routinely used in the technical field can be used for measurement.

According to an embodiment of the present invention, in the composition of the present invention, the mass ratio of the compound of formula (1) or a salt thereof to benzyl alcohol [mass ratio of the compound of formula (1) or a salt thereof:benzyl alcohol] can be, for example, 1:1.9 to 1:20, preferably 1:2.1 to 1:20, more preferably 1:2.2 to 1:10, and further preferably 1:3 to 1:5.

Water

Water to be used in the present invention is not particularly limited, for example, water that is used as a pharmaceutical or food and will be used in the future are included. Examples of water include purified water, ion-exchanged water, distilled water, hyperfiltration water, ultrapure water (for example, milli-Q water), water for injection and saline. Preferably, water for injection is used.

Saccharide

According to an embodiment of the present invention, the composition may further contain a saccharide. Examples of the saccharide include, but are not particularly limited to, saccharides that are used as a pharmaceutical and food and will be used in the future.

The saccharide of the present invention is not particularly limited as long as it does not interfere with the effect of the present invention. Examples of the saccharide include a monosaccharide, a disaccharide, a polysaccharide, a sugar alcohol, and a combination of these. Preferably a monosaccharide, a disaccharide or a sugar alcohol, and more preferably a sugar alcohol is used.

Examples of the monosaccharide include glucose, galactose, mannose, fructose, psicose, allose, sorbose, arabinose, galactosamine, glucosamine, xylose, thioglucose, deoxyribose, fucose, and a combination of these. Preferably glucose is used.

Examples of the disaccharide include lactose, sucrose, maltose, isomaltose, nigerose, kojibiose, trehalose, gentiobiose, cellobiose, sophorose, nigerose, palatinose, melibiose, laminaribiose, and a combination of these. Preferably lactose is used.

Examples of the polysaccharide include dextrin, glycogen, starch, processed starch, and a combination of these. Preferably dextrin or starch is used.

Examples of the sugar alcohol include mannitol, sorbitol, inositol, xylitol, magnesium gluconate, maltitol, meglumine, and a combination of these. Preferably mannitol, and more preferably D-mannitol is used.

According to another embodiment of the present invention, as the saccharide of the present invention, a water-soluble saccharide is preferable. The term "water solubility" of a saccharide that can be used in the present invention refers to a property belonging to "extremely soluble", "easy to dissolve", "slightly easy to dissolve" or "slightly difficult to dissolve", which is defined in the general rule of the 17th revised Japanese Pharmacopoeia. The solubility of a saccharide of the present invention to, for example, water, is about 10 mg/mL or more at normal temperature for handling, for example, room temperature of about 20° C., preferably about 33 mg/mL or more, and more preferably 100 mg/mL or more.

According to a preferred embodiment of the present invention, the content of a saccharide in the composition of the present invention is not particularly limited as long as it does not interfere with the effect of the present invention but the content is, for example, 0.01 to 20 w/v % based on the composition, preferably 0.1 to 10 w/v %, and more preferably 1 to 3 w/v %.

pH Adjuster

According to an embodiment of the present invention, the composition may further contain a pH adjuster. The pH adjuster is not particularly limited. Examples of the pH adjuster includes pH adjusters that are used as a pharmaceutical or food and will be used in the future.

As the pH adjuster herein, a compound suitable for adjusting pH of a liquid composition to be 8 or more, for example, a value later described (for example, pH8 to 11) is used. The pH adjuster may contain a buffer. The buffer herein may be a buffer substance or buffer solution which adjusts pH, which has been changed with an acid or a base, to be a desired pH. Accordingly, the pH adjuster to be contained in the composition of the present invention is not particularly limited as long as it does not interfere with the effect of the present invention. Examples of the pH adjuster include an acid, a base and a buffer.

Examples of the acid include organic acids or inorganic acids. Specific acid include hydrochloric acid, hydrobromic acid, phosphoric acid, sulfuric acid, maleic acid, acetic acid, citric acid, tartaric acid, propionic acid, succinic acid, oxalic acid, lactic acid, malic acid, glutamic acid, pamoic acid, and a combination of these. Preferably, hydrochloric acid, phosphoric acid, acetic acid or citric acid may be used.

Examples of the base include organic bases or inorganic bases. Specific base include sodium hydroxide, potassium hydroxide, ammonia, tromethamine (tris), and a combination of these. Preferably, sodium hydroxide or tromethamine (tris) may be used.

The buffer is not particularly limited as long as it does not interfere with the effect of the present invention. Examples of the buffer include organic acid salts such as an acetate, a lactate, a tartrate, a citrate, a succinate, histidine hydrochloride and a phosphate (for example, potassium phosphate, sodium phosphate); aqueous buffers commonly known in the field of solution preparations such as a citrate buffer (for example, sodium citrate buffer), a tris buffer (for example, tris-HCl buffer), a histidine buffer, an imidazole buffer, a carbonate buffer, a triethanolamine buffer; and a combination of these.

According to a preferred embodiment of the present invention, the concentration of an acid or a base in the composition of the present invention is not particularly limited as long as it does not interfere with the effect of the present invention. The concentration thereof is for example, 0.001 to 2 w/v %, preferably 0.01 to 1.5 w/v %, and more preferably 0.1 to 1 w/v %.

According to a preferred embodiment of the present invention, the concentration of a buffer in the composition of the present invention is not particularly limited as long as it does not interfere with the effect of the present invention. The concentration thereof is, for example, 1 to 500 mM, preferably 5 to 200 mM, and more preferably 10 to 100 mM.

According to an embodiment of the present invention, the composition of the present invention may contain, optionally, a pharmaceutically acceptable additive. Examples of the pharmaceutically acceptable additive include, but are not particularly limited to, an aqueous medium, a solvent, a base, a solubilizing agent, a tonicity agent, a stabilizer, an adjuster, a chelating agent, an excipient, a thickener, a coloring agent, an antioxidant, a dispersant, an emulsifier and a solubilizer. An additive can be blended within the range in which the effect of the present invention is not impaired.

According to an embodiment of the present invention, the dosage form of the composition of the present invention is a liquid. The composition of the present invention contains the compound of formula (1) or a salt thereof, benzyl alcohol and water in combination. The dosage form of the composition is not particularly limited as long as it keeps a characteristics of the combination. The composition can be provided as a dosage form such as an injection, a drip, a syrup or an enema. The dosage form is preferably an injection or a drip. Examples of the injection include, products prepared by filling vials or syringes with the composition of the present invention. Examples of the vial include a single-use vial or a multiple-use vial. Preferably, a multiple-use vial is used. The term "multiple" as used herein, is, for example, 2 to 20 times, and preferably, 3 to 18 times. Note that, if a multiple-use vial is used, it is preferable to maintain preservative effectiveness of the composition of the present invention even after the vial is punctured.

According to an embodiment of the present invention, the composition of the present invention may be a composition for single administration or multiple administration, preferably multiple administration. Examples of the composition include a composition filled in a vial, preferably a composition filled in a multiple-use vial. The term "multiple" is as defined above.

The pH of the composition of the present invention is 8 or more. From the viewpoint of improving solubility of the compound of formula (1) or a salt thereof, the pH is preferably 8 to 11 and more preferably 8 to 10. The timing of measuring pH of the composition of the present invention is not particularly limited and may be during the time of production, storage or use of the composition. The pH of the composition can be measured by a commercially available pH meter (for example, LAQUA F-74, manufactured by HORIBA Ltd.).

According to an embodiment of the present invention, the composition of the present invention can be produced by mixing the compound of formula (1) or a salt thereof, water and benzyl alcohol, optionally, another solvent in accordance with a method commonly known in the technical field. Since the composition of the present invention may further contain a saccharide and, optionally, a pH adjuster, the composition of the present invention can be produced by mixing the compound of formula (1) or a salt thereof, water, benzyl alcohol, a saccharide and, optionally, a pH adjuster and/or another solvent in accordance with a method commonly known in the technical field. For example, the composition of the present invention is produced by mixing/dissolving the compound of formula (1) or a salt thereof, water and benzyl alcohol and, optionally, another solvent in accordance with a method commonly known in the technical field. More specifically, the composition of the present invention is produced, for example, by a method (A) in which the compound of formula (1) or a salt thereof, benzyl alcohol, a saccharide and a pH adjuster are mixed, and then, water is added; a method (B) in which water, benzyl alcohol, a saccharide and a pH adjuster are mixed, and then, the compound of formula (1) or a salt thereof is added; or a method (C) in which water, benzyl alcohol and the compound of formula (1) or a salt thereof are mixed, and then, a saccharide and a pH adjuster are added. In producing the composition of the present invention, the mixture may be subjected to homogenization and sterilization processes as long as the effect of the present invention is not impaired.

The another solvent to be used for producing the composition of the present invention, is not particularly limited and a solvent that is used as a pharmaceutical or food and will be used in the future may be included. Examples of the another solvent include alcohols (for example, methanol, ethanol, propanol, propylene glycol), organic acids (for example, acetic acid, propionic acid), polyethylene glycol, and a mixed solvent of these.

Composition

According to an embodiment of the present invention, it is possible to effectively enhance the preservative effectiveness of the composition of the present invention which is the liquid composition containing the compound of formula (1) of the present invention or a salt thereof. It is preferable that the preservative effectiveness complies with at least one of the standards defined in USP (for example, USP43-NF38-S2), European Pharmacopoeia (for example, Ph.Eur.10.4) and Japanese Pharmacopoeia (for example, Japanese Pharmacopoeia 17th edition, Japanese Pharmacopoeia 18th edition). Specifically, it is determined that the preservative effectiveness against, e.g., bacteria, is present if the viable count of bacterial cells decreases from $10^5$ to $10^6$ per the liquid composition of the present invention (1 ml or 1 g) to, for example, $10^2$ to $10^3$ or less, after 24 hours, preferably $10^1$ to $10^2$ or less, and more preferably $10^1$ or less. It is determined that the preservative effectiveness against, e.g., fungi is present if the viable count of fungus cells per the liquid composition of the present invention (1 ml or 1 g) decreases from $10^5$ to $10^6$ to, for example, $10^3$ to $10^4$ or less after 7 days, preferably $10^2$ to $10^3$ or less, and more preferably $10^1$ or less. A test for preservative effectiveness can be carried out in accordance with the preservative effectiveness test specified in USP43-NF38-S2 General Chapter<51> or Ph.Eur.10.4 General Chapter 5.1.3, in similar conditions disclosed, for example, in Experimental Examples 1, 3 and 4.

According to an embodiment of the present invention, the subject against which the above preservative effectiveness is shown is not particularly limited, but include, for example, bacteria and/or fungi. Examples of the bacteria include *Escherichia coli, Pseudomonas aeruginosa* and *Staphylococcus aureus*. Examples of the fungi include *Candida albicans* and *Aspergillus brasiliensis*.

According to an embodiment of the present invention, the composition of the present invention containing the compound of formula (1) or a salt thereof and benzyl alcohol in combination can be used continuously or discontinuously for a long period of time by enhancing preservative effectiveness thereof. Specifically, the composition of the present invention can be used, for example, one day or more, preferably 7 days or more, more preferably 14 days or more, further preferably 21 days or more, and further preferably 28 days or more. The upper limit is not particularly limited but preferably 40 days or less.

Kit

According to another embodiment of the present invention, there is provided a kit for producing the composition of the present invention disclosed above consisting of a first composition containing the compound of formula (1) or a salt thereof and a second composition containing benzyl alcohol and water.

According to a preferred embodiment of the present invention, the first composition contains a saccharide and, optionally, a pH adjuster. The first composition may have, optionally, a pharmaceutically acceptable additive. The saccharides, pH adjuster and pharmaceutically acceptable additive herein are the same as defined above. The first composition is preferably lyophilized.

According to a further preferred embodiment of the present invention, the first composition is filled in a vial. Examples of the vial include, a single-use vial and a multiple-use vial. Preferably, a multiple-use vial is used. The "multiple" refers to, for example, 2 to 20 times, and preferably, 3 to 18 times. Note that, if a multiple-use vial is used, preservative effectiveness of the composition of the present invention is preferably maintained even after the vial is punctured.

According to another preferred embodiment of the present invention, the content of benzyl alcohol in the second composition is, for example, 0.9 to 5 w/v % based on the whole second composition or the whole composition of the present invention, preferably 0.9 to 4 w/v %, more preferably 0.9 to 3 w/v %, and further preferably 1.2 to 2 w/v %.

According to another embodiment of the present invention, there is provided a method for producing the composition of the present invention, including mixing a first composition containing the compound of formula (1) or a salt thereof and a second composition containing benzyl alcohol and water. As the method, more specifically, if a first composition is filled in a vial, e.g., a method including adding a second composition to the vial to mix the first composition and the second composition is mentioned. The first composition herein is preferably lyophilized. Accordingly, the production method may be a method of reconstituting a first composition containing the compound of formula (1) or a salt thereof with benzyl alcohol and water contained in a second composition.

According to an embodiment of the present invention, a first composition may be produced by a method of mixing/ dissolving the compound of formula (1) or a salt thereof and a solvent in accordance with a method commonly known in the technical field. As described above, the first composition is preferably lyophilized. Since the first composition may contain a saccharide and, optionally, a pH adjuster, the first composition may be produced by mixing/dissolving the compound of formula (1) or a salt thereof, a saccharide, optionally, a pH adjuster and a solvent (for example, water and/or another solvent) in accordance with a method commonly known in the technical field. For example, the first composition can be produced by mixing/dissolving the compound of formula (1) or a salt thereof, a saccharide and a pH adjuster in water and/or another solvent in accordance with a method commonly known in the technical field. More specifically, the first composition of the present invention is produced, for example, by a method (A) in which the compound of formula (1) or a salt thereof, a saccharide and a pH adjuster are mixed, and then, water is added, a method (B) in which water, a saccharide and a pH adjuster are mixed, and then, the compound of formula (1) or a salt thereof is added, or a method (C) in which water and the compound of formula (1) or a salt thereof are mixed, and then a saccharide and a pH adjuster are added. Thereafter, if necessary, the solution obtained by any one of the aforementioned methods can be lyophilized. In producing the first composition, the first composition may be subjected to homogenization and sterilization processes as long as the effect of the present invention is not impaired.

Another solvent to be used for production of the first composition is the same as defined as another solvent to be used for producing the composition of the present invention.

According to another embodiment of the present invention, the second composition can be produced by mixing benzyl alcohol and water in accordance with a method commonly known in the technical field. In producing the second composition, the second composition may be subjected to homogenization and sterilization processes as long as the effect of the present invention is not impaired.

According to an embodiment of the present invention, the composition of the present invention or first composition can be widely applied to diseases, disease conditions or symptoms in which inflammatory cells (for example, granulocytes (neutrophil, eosinophil, basophil), lymphocytes (for example, T lymphocytes, NK cells), monocytes, macrophages, plasma cells, mast cells, platelets) are involved. Examples of the diseases, disease conditions or symptoms include pancreatitis, surgical invasion, disseminated intravascular coagulation (DIC), neoplastic disease, pyometra, heatstroke, immune-mediated hemolytic anemia (IMHA), sepsis, angiosarcoma, gastric volvulus, ischemia reperfusion injury, purpura, liver failure, hepatitis, pneumonia, systemic inflammatory response syndrome (SIRS), external wounds, osteoarthritis, cystitis, intervertebral disc disease, atopic/allergy, dermatitis, immune-mediated disease, otitis, inflammatory bowel disease, chronic pain, colitis, chronic obstructive pulmonary disease (COPD), cholecystitis, cholangitis). Advantageously, the composition of the present invention or first composition can provide a therapeutic and preventive effect on, e.g., pancreatitis, surgical invasion and disseminated intravascular coagulation (DIC). Thus, according to another embodiment of the present invention, the composition of the present invention or first composition is provided as a composition for treating or preventing diseases, disease conditions or symptoms in which inflammatory cells are involved, preferably, pancreatitis, surgical invasion or disseminated intravascular coagulation (DIC). The composition of the present invention or first composition can be used as a pharmaceutical product or quasi-drug for humans or animals. The composition of the present invention or first composition may be appropriately used, if necessary, in combination with another pharmaceutical product or quasi-drug commonly used in this technical field. Note that, when the first composition is applied, it is preferably used together with water and benzyl alcohol.

According to an embodiment of the present invention, the subject to which the composition of the present invention is to be applied is, for example, an animal, preferably, a non-human animal such as a mammal, a bird, a reptile, an amphibian and fish, and more preferably, a mouse, a rat, a rabbit, a dog, a cat, a pig, a cow and a horse. The animal may be a farm animal, a pet, a human-reared animal, a wild animal and a racing animal. The subject may be a healthy person (healthy animal) or a patient (sick animal). If the composition of the present invention is composition for multiple administration, for example, if the composition of the present invention is filled in a multiple-use vial, the subject to which the composition is administered a plurality of times may be the same individual or different individuals (i.e., a plurality of individuals).

According to another embodiment of the present invention, there is provided a method for treating or preventing diseases, disease conditions or symptoms in which inflammatory cells of a subject are involved, preferably, pancreatitis, surgical invasion or disseminated intravascular coagulation (DIC), including administering the composition of the present invention to the subject. According to a further another embodiment of the present invention, the method for treating or preventing diseases, disease conditions or symptoms in which inflammatory cells of a subject are involved is, if the subject is healthy, defined as a non-therapeutic method excluding a medical practice. The method for treating or preventing diseases, disease conditions or symptoms in which inflammatory cells of a subject are involved, can be carried out in accordance with the content disclosed in the specification with respect to the composition of the present invention.

The effective amount of the compound of formula (1) of the present invention or a salt thereof and frequency of administration of the composition of the present invention are not particularly limited and appropriately determined by those skilled in the art depending on the type and purity of the compound of formula (1) or a salt thereof, the dosage form of the composition, the type, nature, sex, age and symptom of the subject. For example, the effective amount of the compound of formula (1) or a salt thereof is 0.01 to 1000 mg/body weight (kg) and preferably 0.05 to 500 mg/body weight (kg). The frequency of administration per the same individual is, for example, 1 to 5 times per day, preferably 1 to 3 times per day, and more preferably once to twice per day. The period for administration per the same individual is, for example, 1 to 7 days, preferably 1 to 5 days, and more preferably 1 to 3 days.

According to another embodiment of the present invention, there is provided use of the compound of formula (1) or a salt thereof, benzyl alcohol and water in combination for producing a liquid composition having pH of 8 or more. According to another preferred embodiment of the present invention, the above composition is used for treating or preventing diseases, disease conditions or symptoms in which inflammatory cells are involved, preferably, pancreatitis, surgical invasion, or disseminated intravascular coagulation (DIC).

According to another embodiment of the present invention, there is provided use of the compound of formula (1)

or a salt thereof and benzyl alcohol in combination for enhancing preservative effectiveness of a liquid composition having pH of 8 or more. According to another preferred embodiment of the present invention, there is provided use of the above components in combination for treating or preventing diseases, disease conditions or symptoms in which inflammatory cells are involved, preferably, pancreatitis, surgical invasion or disseminated intravascular coagulation (DIC).

According to another embodiment of the present invention, there is provided a composition of the compound of formula (1) or a salt thereof, benzyl alcohol for enhancing preservative effectiveness of a liquid composition having pH of 8 or more. According to another preferred embodiment of the present invention, there is provided the composition for treating or preventing diseases, disease conditions or symptoms in which inflammatory cells are involved, preferably, pancreatitis, surgical invasion, or disseminated intravascular coagulation (DIC).

According to another embodiment of the present invention, there is provided a method for enhancing preservative effectiveness of the liquid composition containing the compound of formula (1) or a salt thereof, allowing the compound of formula (1) or a salt thereof and benzyl alcohol to coexist in a liquid composition and adjusting pH of the liquid composition to be 8 or more. The preservative effectiveness used herein is preferably preservative effectiveness against bacteria and/or fungi.

The embodiments of the use, combination and composition each can be carried out in accordance with the disclosure of the composition and method of the present invention.

EXAMPLES

Now, the present invention will be more specifically described by way of the following Experimental Examples, but the technical scope of the present invention is not limited by these examples. Unless otherwise specified, units and measuring methods disclosed herein follow the JIS standard.

Substances used in Experimental Examples are as follows.

- Compound 1: N-(2-ethylsulfonylamino-5-trifluoromethyl-3-pyridyl)cyclohexanecarboxamide, monosodium salt, monohydrate (Fuzapladib sodium hydrate)
- D-mannitol: manufactured by Nacalai Tesque Inc. (Experimental Examples 1, 2), manufactured by Roquette Freres (Experimental Examples 3, 4)
- Tromethamine: manufactured by Nacalai Tesque Inc. (Experimental Examples 1, 2), manufactured by Biospectra, Inc. (Experimental Examples 3, 4)
- Benzyl alcohol: manufactured by Spectrum Chemical Manufacturing Crop. (Experimental Examples 1, 2), manufactured by Lanxess Deutschland GmbH (Experimental Examples 3, 4)

Apparatuses used in Experimental Examples are as follows.

- Magnetic stirrer: Pasolina Mini Stirrer CT-1AT, manufactured by AS ONE Corporation (Experimental Examples 1, 2)
- High Shear Mixer: BX-60, manufactured by Silverson (Experimental Examples 3, 4)
- pH meter: LAQUA F-74, manufactured by HORIBA Ltd.
- Sterile filter: DISMIC-25AS, manufactured by ADVANTEC (Experimental Examples 1, 2), KA2EKVP1G, manufactured by Pall Manufacturing Ltd. (Experimental Examples 3, 4)

Experimental Examples 1: Antibacterial Evaluation of Compound 1-Containing Liquid Composition (1)

(a) Preparation of Liquid Composition (experimental plot 1 to 4)

One or more substances selected from compound 1, D-mannitol, tromethamine and benzyl alcohol were put in a 20 mL screw-cap bottle and weighed. Water for injection (15 mL) was poured in the bottle and mixed/dissolved by a magnetic stirrer. Thereafter, 0.1 M HCl or 0.1 M NaOH was added to adjust pH to the corresponding value shown in Table 1. The resultant solution was transferred to a 20 mL measuring flask and water for injection was added up to 20 mL. Thereafter, the solution was homogenized and passed through a sterile filter. In this manner, liquid compositions of the experimental plots shown in Table 1 were obtained.

(b) Antibacterial Evaluation of Compound 1-Containing Liquid Composition

Antibacterial evaluation was carried out with reference to preservative effectiveness test (Efficacy of Antimicrobial Preservation) of the European Pharmacopeia 9.0, as follows. A stock solution of *Escherichia coli* (hereinafter referred to also as *E. coli*) was prepared using Luria Bertani medium (viable count $4.08\times10^7$ per *E. coli* stock solution (1 mL)). Thereafter, *E. coli* stock solution (5 μL) was inoculated/mixed in the liquid composition (500 μL) prepared in the step (a) and stored at 20 to 25° C. under dark conditions. Twenty four hours after inoculation, the number of living cells (viable count) was determined. Note that, as the viable count at 0 hours after bacterial inoculation, the viable count immediately after the *E. coli* stock solution was inoculated/mixed in saline, was employed.

TABLE 1

| | | Experimental plot | | | | |
|---|---|---|---|---|---|---|
| | | 1 | 2 | 3 | 4 | Saline |
| Compound 1 (w/v %) | | 0.4 | 0.4 | — | 0.4 | — |
| D-mannitol (w/v %) | | 1.5 | 1.5 | — | — | |
| Tromethamine (w/v %) | | 0.6 | 0.6 | — | — | |
| Benzyl alcohol (w/v %) | | 0.9 | — | 0.9 | 0.9 | |
| pH | | 8.7 | 8.7 | 8.8 | 8.7 | — |
| Viable (cells/mL) count | 0 hr. after inoculation | — | — | — | — | $4.08\times10^5$ |
| | 24 hr. after inoculation | 0 | $1.69\times10^5$ | $8.90\times10^3$ | 0 | — |

In the case (experimental plot 3) containing benzyl alcohol alone at pH8.7 to 8.8, living cells remained 24 hours after inoculation. It was found that the antibacterial efficacy (i.e., preservative effectiveness) of this case was not sufficient. However, in the cases (experimental plot 1 and 4) where benzyl alcohol and compound 1 were mixed, the vial count 24 hours after inoculation was 0. It was found that antibacterial efficacy was significantly enhanced.

Experimental Example 2: Antibacterial Evaluation of Compound 1-Containing Liquid Composition (2)

(a) Preparation of Liquid Composition (Experimental Plot 5 to 10)

One or more substances selected from compound 1, D-mannitol, tromethamine and benzyl alcohol were put in a 20 mL screw-cap bottle and weighed. Water for injection (15 mL) was poured in the bottle and mixed/dissolved by a magnetic stirrer. Thereafter, 0.1 M HCl or 0.1 M NaOH was added to adjust pH to the corresponding value shown in Table 2. The resultant solution was transferred to a 20 mL measuring flask and water for injection was added up to 20 mL. Thereafter, the solution was homogenized and passed through a sterile filter. In this manner, liquid compositions of the experimental plots shown in Table 2 were obtained.

(b) Antibacterial Evaluation of Compound 1-Containing Liquid Composition

Antibacterial evaluation was carried out with reference to preservative effectiveness test (Efficacy of Antimicrobial Preservation) of the European Pharmacopeia 9.0, as follows. A stock solution of *Escherichia coli* (hereinafter referred to also as *E. coli*) was prepared in the same manner as in Experimental Example 1 (viable count $9.90\times10^7$ per *E. coli* stock solution (1 mL)). Thereafter, *E. coli* stock solution (5 μL) was inoculated/mixed in the liquid composition (500 μL) prepared in the step (a) and stored at 20 to 25° C. under dark conditions. Twenty four hours after inoculation, the number of living cells (viable count) was determined. Note that, the viable count at 0 hours after bacterial inoculation was determined immediately after the *E. coli* stock solution was inoculated/mixed in saline. Note that, as the viable count at 0 hours after bacterial inoculation, the viable count immediately after the *E. coli* stock solution was inoculated/mixed in saline, was employed.

TABLE 2

| | | Experimental plot | | | | | | |
|---|---|---|---|---|---|---|---|---|
| | | 5 | 6 | 7 | 8 | 9 | 10 | Saline |
| Compound 1 (w/v %) | | — | — | 0.4 | 0.4 | — | 0.4 | — |
| D-mannitol (w/v %) | | — | — | — | — | — | 1.5 | |
| Tromethamine (w/v %) | | — | — | — | — | — | 0.6 | |
| Benzyl alcohol (w/v %) | | 0.9 | 0.9 | — | 0.9 | 0.8 | 0.8 | |
| pH | | 4.9 | 8.7 | 8.7 | 8.7 | 8.7 | 8.7 | — |
| Viable count (cells/mL) | 0 hr. after inoculation | — | — | — | — | — | — | $9.90\times10^5$ |
| | 24 hr. after inoculation | 0 | $6.70\times10^4$ | $8.00\times10^5$ | 0 | $3.64\times10^5$ | $5.00\times10^2$ | — |

In the cases containing benzyl alcohol alone, antibacterial efficacy was shown at pH4.9 (experimental plot 5), but virtually no antibacterial efficacy was shown at pH8.7 (experimental plot 6). Also, in the case (experimental plot 7) containing compound 1 alone at pH8.7, virtually no antibacterial efficacy was shown. However, in the case containing benzyl alcohol and compound 1 in combination (experimental plot 8), viable count 24 hours after inoculation pH8.7 was 0. It was found that antibacterial efficacy was significantly enhanced.

Experimental Example 3: Antibacterial Evaluation of Compound 1-Containing Liquid Composition (3)

(a) Preparation of Lyophilized Preparation

Compound 1 (160 g), D-mannitol (600 g), tromethamine (240 g) and water (17 kg) were mixed. After pH of the mixture was adjusted to be pH8.7 with 1 M hydrochloric acid, water was added to the mixture up to 20 L. The resultant mixture was filtered/sterilized by a 0.2 μm filter. A vial is load with 1.75 mL of the filtrate, capped half with a rubber stopper and lyophilized. After lyophilization, the vial was fully capped with the rubber stopper and wrapped with aluminum seal to obtain a lyophilized preparation.

(b) Preparation of Liquid Composition

Into the vial obtained in the step (a), water for injection (3.5 mL) containing 1.8 w/v % benzyl alcohol was injected by a syringe with a 20-gauge needle. In this manner, the lyophilized preparation was reconstituted to obtain a liquid composition.

(c) Storage of Liquid Composition

Each of the vials was punctured by a syringe with a 20-gauge needle to take out about 0.05 mL of a drug solution. The syringe was replaced with a new one every puncture, puncture was repeated twice. The vials were stored at room temperature. On day 2 and day 3, the vials were taken out and punctured once by a syringe with a 20-gauge needle to take out about 0.05 mL of the drug solution. Thereafter the vials were stored at room temperature for a predetermined period of time.

(d) pH Measurement and Antibacterial Evaluation of Compound 1-Containing Liquid Composition Immediately after reconstitution, pH was measured. On day 8, pH measurement and antibacterial evaluation were carried out.

The pH measurement was carried out in accordance with the glass electrode method.

The antibacterial evaluation was carried out in accordance with the preservative effectiveness test specified in USP43-NF38-S2 General Chapter <51> and Ph.Eur.10.4 General Chapter 5.1.3. The test microbes used in this Experimental Example were bacteria, which were *Staphylococcus aureus* (*S. aureus*), *Pseudomonas aeruginosa* (*P. aeruginosa*) and *Escherichia coli* (*E. coli*); and fungi, which were *Candida albicans* (*C. albicans*) and *Aspergillus brasiliensis* (*A. brasiliensis*). The test microbes were inoculated to/mixed with the liquid compositions prepared and stored in the step (b) and incubated at 20 to 25° C. At 0 hours, 6 hours, 24 hours, Day 7, Day 14 and Day 28 after inoculation, the number of colony-forming units (CFU/mL) was counted. Note that, the number of microbes to be inoculated was controlled such that the number of colony-forming units (CFU/mL) after inoculation in a suspension became $1\times10^5$ to $1\times10^6$. Evaluation was made based on the USP acceptance criteria for injections and other parenteral agents and Ph. Eur. acceptance criteria for parenteral preparations shown in Tables below.

TABLE 3

| USP acceptance criteria for injections and other parenteral agents | | | |
|---|---|---|---|
| | Day 7 | Day 14 | Day 28 |
| Bacteria | Logarithmic decrement of 1.0 from initial count | Logarithmic decrement of 3.0 from initial count | No increase from Day 14 count |
| Fungi | No increase from initial count | No increase from initial count | No increase from initial count |

TABLE 4

| Ph. Eur. acceptance criteria for parenteral preparations Logarithmic decrement | | | | | | |
|---|---|---|---|---|---|---|
| | Criterium | 6 hours | 24 hours | Day 7 | Day 14 | Day 28 |
| Bacteria | A | 2 | 3 | | | NR |
| | B | | 1 | 3 | | NI |
| Fungi | A | | | 2 | | NI |
| | B | | | | 1 | NI |

*NI: no increase in number of viable microbe cells compared to previous measurement.
*NR: no recovery of specified microbe.

Test Results 1. pH of liquid composition

The pH of a liquid composition immediately after reconstitution was 8.7 and the pH thereof after storage for 8 days was 8.7.

2. Antibacterial activity of liquid composition after storage for 8 days.

The results are shown in the Table below. The liquid composition of this example complied with the USP acceptance criteria for injections and other parenteral agents and Ph. Eur. acceptance criteria for parenteral preparations.

TABLE 5

| Test microbe | Number of inoculated cells (CFU/mL) | Logarithmic decrement 0 hours | 6 hours | 24 hours | Day 7 | Day 14 | Day 28 | Criterium USP | Ph. Eur. |
|---|---|---|---|---|---|---|---|---|---|
| *S.aureus* | $3.3 \times 10^5$ | 1.4 | 4.2 | >4.5 | >4.5 | >4.5 | >4.5 | Pass | A |
| *P.aeruginosa* | $1.5 \times 10^5$ | >4.2 | >4.2 | >4.2 | >4.2 | >4.2 | >4.2 | Pass | A |
| *E.coli* | $9.6 \times 10^5$ | >5.0 | >5.0 | >5.0 | >5.0 | >5.0 | >5.0 | Pass | *NC |
| *C.albicans* | $4.2 \times 10^5$ | 1.6 | 3.0 | >4.6 | >4.6 | >4.6 | >4.6 | Pass | A |
| *A.brasiliensis* | $2.3 \times 10^5$ | 0.0 | 0.1 | 2.5 | >4.4 | >4.4 | >4.4 | Pass | A |

*NC: According to Ph.Eur. 5.1.3, *E. coli* is not identified as challenge microbe.

Experimental Example 4: Antibacterial Evaluation of Compound 1-Containing Liquid Composition (4)

(a) Preparation of Lyophilized Preparation

Compound 1 (160 g), D-mannitol (600 g), tromethamine (240 g) and water (17 kg) were mixed. After pH of the mixture was adjusted to be pH8.7 with 1 M hydrochloric acid, water was added to the mixture up to 20 L. The resultant mixture was filtered/sterilized by a 0.2 μm filter. A vial is loaded with 1.75 mL of the filtrate, capped half with a rubber stopper, and lyophilized. After lyophilization, the vial was fully capped with the rubber stopper and wrapped with aluminum seal to obtain a lyophilized preparation.

(b) Preparation of Liquid Composition

Into the vial obtained in the step (a), water for injection (3.5 mL) containing 1.8 w/v % benzyl alcohol was injected by a syringe with a 20-gauge needle. In this manner, the lyophilized preparation was reconstituted to obtain a liquid composition.

(c) Storage of Liquid Composition

Each of the vials was punctured by a syringe with a 20-gauge needle to take out about 0.05 mL of a drug solution. The syringe was replaced with a new one every puncture, puncture was repeated twice. The vials were stored in a refrigerator (2 to 8° C.). The vials were taken out from the refrigerator once a day from Day 2 to Day 13 and punctured by a syringe with a 20-gauge needle to take out about 0.05 mL of a drug solution. Thereafter, the vials were stored in the refrigerator for a predetermined period.

(d) pH Measurement and Antibacterial Evaluation of Compound 1-Containing Liquid Composition Immediately after the reconstitution, pH was measured. On day 29, the vials were taken out from the refrigerator and pH measurement and antibacterial evaluation were carried out. The pH measurement was carried out in accordance with the glass electrode method. The antibacterial evaluation was carried out in accordance with the preservative effectiveness test specified in USP43-NF38-S2 General Chapter<51> and Ph.Eur.10.4 General Chapter 5.1.3. The test microbes used in this Experimental Example were bacteria, which were *Staphylococcus aureus* (*S. aureus*), *Pseudomonas aeruginosa* (*P. aeruginosa*) and *Escherichia coli* (*E. coli*); and fungi, which were *Candida albicans* (*C. albicans*) and *Aspergillus brasiliensis* (*A. brasiliensis*). The test microbes were inoculated/mixed to the liquid compositions prepared and stored in the step (b) and incubated at 20 to 25° C. At 0 hours, 6 hours, 24 hours, Day 7, Day 14 and Day 28 after inoculation, the number of colony-forming units (CFU/mL) was counted. Note that, the number of microbial cells to be inoculated was controlled such that the number pf colony-forming units (CFU/mL) after inoculation in a suspension became $1\times10^5$ to $1\times10^6$. Evaluation was made based on the same criteria as in Experimental Example 3.

Test results 1. pH of liquid composition

The pH of a liquid composition immediately after reconstitution was 8.7 and the pH thereof after storage for 29 days was 8.7.

2. Antibacterial activity of liquid composition after storage for 29 days

The results are shown in the Table below. As shown in the Table, the liquid composition of this example complied with the USP acceptance criteria for injections and other parenteral agents and Ph. Eur. acceptance criteria for parenteral preparations.

TABLE 6

| | Number of inoculated | Logarithmic decrement | | | | | | Criterium | |
|---|---|---|---|---|---|---|---|---|---|
| | cells | 0 | 6 | 24 | Day | Day | Day | | |
| Test microbe | (CFU/mL) | hours | hours | hours | 7 | 14 | 28 | USP | Ph.Eur. |
| *S.aureus* | $4.0 \times 10^5$ | 1.1 | >4.6 | >4.6 | >4.6 | >4.6 | >4.6 | Pass | A |
| *P.aeruginosa* | $1.5 \times 10^5$ | >4.2 | >4.2 | >4.2 | >4.2 | >4.2 | >4.2 | Pass | A |
| *E.coli* | $9.1 \times 10^5$ | >5.0 | >5.0 | >5.0 | >5.0 | >5.0 | >5.0 | Pass | *NC |
| *C.albicans* | $3.9 \times 10^5$ | 1.0 | 3.0 | 4.6 | >4.6 | >4.6 | >4.6 | Pass | A |
| *A.brasiliensis* | $2.4 \times 10^5$ | 0.0 | 0.2 | 3.2 | >4.4 | >4.4 | >4.4 | Pass | A |

*NC: According to Ph.Eur. 5.1.3, *E. coli* is not identified as challenge microbe.

The invention claimed is:

1. A liquid composition comprising:

a compound represented by formula (1) or a salt thereof:

[Formula 1]

(1)

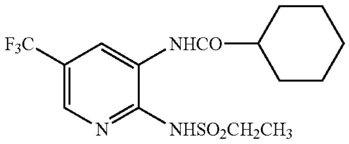

benzyl alcohol; and water, wherein the composition has a pH of 8 or more.

2. The composition according to claim 1, further comprising a saccharide and, optionally, a pH adjuster.

3. The composition according to claim 2, wherein the saccharide is at least one selected from the group consisting of a monosaccharide, a disaccharide, a polysaccharide, and a sugar alcohol.

4. The composition according to claim 2, wherein the pH adjuster is a buffer.

5. The composition according to claim 1, wherein a content of benzyl alcohol in the liquid composition is 0.9 to 3 w/v %.

6. The composition according to claim 1, wherein a content of the compound of formula (1) or a salt thereof in the liquid composition is 0.01 to 1 w/v %.

7. The composition according to claim 1, for multiple administration.

8. A kit for producing the composition according to claim 1, comprising:

a first composition containing the compound of formula (1) or a salt thereof; and a second composition containing benzyl alcohol and water.

9. The kit according to claim 8, wherein the first composition contains a saccharide and, optionally, a pH adjuster.

10. The kit according to claim 8, wherein a content of benzyl alcohol in the second composition is 0.9 to 3 w/v % based on the second composition.

11. The kit according to claim 1, wherein the first composition is filled in a vial.

12. The kit according to claim 11, wherein the vial is a single-use vial or a multiple-use vial.

13. A method for producing the composition according to claim 1, comprising mixing a first composition containing the compound of formula (1) or a salt thereof, and a second composition containing benzyl alcohol and water.

14. A method for enhancing the preservative effectiveness of a liquid composition comprising the compound of formula (1) or a salt thereof according to claim 1, comprising:

1) Allowing the compound of formula (1) or a salt thereof and benzyl alcohol to be present together in the liquid composition, and 2) adjusting the pH of the liquid composition to be 8 or more.

* * * * *